US009074996B2

(12) United States Patent
Yamashita et al.

(10) Patent No.: US 9,074,996 B2
(45) Date of Patent: Jul. 7, 2015

(54) LIQUID COMPONENT SENSOR (71) Applicant: DENSO CORPORATION, Kariya, Aichi-pref. (JP)

(72) Inventors: Shuichi Yamashita, Okazaki (JP); Hiroyuki Wado, Toyota (JP); Takayuki Matsui, Nisshin (JP); Atsushi Miura, Nagoya (JP)

(73) Assignee: DENSO CORPORATION, Kariya (JP)

( * ) Notice: Subject to any disclaimer, the term of this patent is extended or adjusted under 35 U.S.C. 154(b) by 174 days.

(21) Appl. No.: 13/905,268

(22) Filed: May 30, 2013

(65) Prior Publication Data
US 2013/0320214 A1  Dec. 5, 2013

(30) Foreign Application Priority Data

Jun. 1, 2012  (JP) .................................. 2012-126257

(51) Int. Cl.
*G01J 5/20* (2006.01)
*G01N 21/27* (2006.01)
*G01N 21/03* (2006.01)
*G01N 21/3577* (2014.01)

(52) U.S. Cl.
CPC ............ *G01N 21/27* (2013.01); *G01N 21/0303* (2013.01); *G01N 21/3577* (2013.01)

(58) Field of Classification Search
CPC .......................................................... G01J 5/20
USPC ........................................................ 250/338.4
See application file for complete search history.

(56) References Cited

U.S. PATENT DOCUMENTS

| 7,371,562 B2* | 5/2008 | Cunningham et al. ...... 435/287.1 |
| 2006/0119843 A1* | 6/2006 | O'Connell .................... 356/246 |
| 2009/0165876 A1* | 7/2009 | Atkin et al. .................... 137/825 |

FOREIGN PATENT DOCUMENTS

| JP | 2000-121547 A | 4/2000 |
| JP | 2010-078544 A | 4/2010 |

OTHER PUBLICATIONS

Blomberg, Lehto and Torkkeli, Electrically Tuneable Micromachined Fabry-Perot Interferometer in Gas Analysis, Physica Scripta,1997, pp. 119-121, vol. T69, Vaisala Oy, Helsinki, Finland.

* cited by examiner

*Primary Examiner* — David Porta
*Assistant Examiner* — Hugh H Mapin
(74) *Attorney, Agent, or Firm* — Posz Law Group, PLC (57) ABSTRACT A liquid component sensor includes: an infrared light source; a detection cell including: two substrates made of material for penetrating an infrared light therethrough and stacked each other; a passage for flowing liquid arranged between facing surfaces of the substrates; and a detection portion for detecting the liquid provided by at least a part of the passage; a spectrometer for dispersing light penetrating the detection cell; and a light detector for detecting dispersed light. Each substrate includes outside and facing surfaces, so that two substrates provide four surfaces totally. The detection cell further includes a filter for passing the infrared light having a predetermined wavelength selectively. The filter is disposed on at least one of four surfaces at a predetermined position, which corresponds to at least the detection portion.

9 Claims, 7 Drawing Sheets

FIG. 15

LIQUID COMPONENT SENSOR

CROSS REFERENCE TO RELATED APPLICATION

This application is based on Japanese Patent Application No. 2012-126257 filed on Jun. 1, 2012, the disclosure of which is incorporated herein by reference.

TECHNICAL FIELD

The present disclosure relates to a liquid component sensor for detecting at least one of a component and a concentration of the component in liquid with using infrared light.

BACKGROUND

Conventionally, as described in JP-A-2000-121547, a detection cell as a detecting cell for detecting a component and/or a concentration of the component in liquid sample with using light is well known.

The detection cell includes two glass plates as two substrates, which are stacked. Further, the cell includes a fluid passage as a pathway for flowing the liquid sample. The fluid passage is formed between one surface of one glass plate and a facing surface of the other glass plate.

Here, the liquid such as gasoline, water, alcohol such as ethanol and acetic acid has absorption wavelength in mid-infrared zone between three micrometers and ten micrometers. Thus, with using the detection cell described in JP-A-2000-121547, a liquid component sensor with using infrared light is provided. Thus, the sensor detects the component and/or the concentration of the component in liquid.

However, when the detection cell is used as the component sensor, the liquid component sensor necessarily includes an infrared light source for irradiating the infrared light, a filter for passing the infrared light having a predetermined wavelength therethrough (i.e., the filter filtering the infrared light selectively in the wavelength, a spectrometer for executing spectrum analysis of light penetrated through the detection cell (i.e., the spectrometer dispersing light), and a light detector for detecting dispersed light in addition to the detection cell. Further, it is necessary to arrange the filter, the detection cell and the spectrometer between the infrared light source and the light detector with high accuracy in position. Accordingly, the number of elements in the sensor is large, and the detection accuracy may be reduced if the position of each element is deviated from a proper position.

SUMMARY

It is an object of the present disclosure to provide a liquid component sensor for detecting at least one of a component and a concentration of the component in liquid with using infrared light. In the liquid component sensor, the number of elements is reduced, and the detection accuracy is not reduced too much even if the position of each element is deviated from a proper position.

According to an example aspect of the present disclosure, a liquid component sensor includes: an infrared light source; a detection cell, which includes: a pair of substrates made of material for penetrating an infrared light therethrough and stacked each other; a passage for flowing liquid arranged between facing surfaces of the substrates; and a detection portion for detecting the liquid provided by at least a part of the passage; a spectrometer for dispersing light penetrating the detection cell; and a light detector for detecting dispersed light. Each substrate includes an outside surface and the facing surface, which faces another substrate, and the outside surface is opposite to the facing surface, so that the pair of substrates provide four surfaces totally. The detection cell further includes a filter for passing the infrared light having a predetermined wavelength selectively. The filter is disposed on at least one of four surfaces at a predetermined position, which corresponds to at least the detection portion.

In the above sensor, the filter is a part of the detection cell. Thus, the number of elements in the sensor is minimized, compared with a conventional detection cell. Further, a position deviation of the filter when the sensor is assembled is restricted, compared with a case where the filter is assembled on the detection cell as a separate element. Thus, the detection accuracy reduction caused by the position deviation is limited. Therefore, the assembling of the sensor is simplified.

BRIEF DESCRIPTION OF THE DRAWINGS

The above and other objects, features and advantages of the present disclosure will become more apparent from the following detailed description made with reference to the accompanying drawings. In the drawings.

DETAILED DESCRIPTION

A optical liquid component sensor according to an example embodiment is used for detecting a component and a concentration of the component in liquid. For example, when gasoline and alcohol such as ethanol are mixed into a mixed fuel, the sensor is used as a fuel property sensor for detecting alcohol, water and acetic acid in the gasoline.

Figure 1:
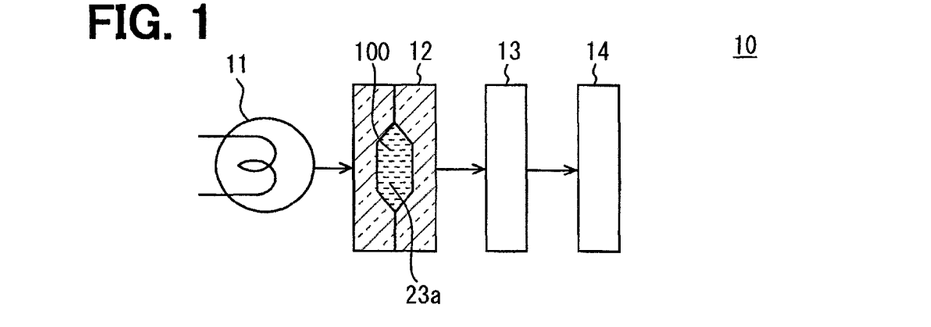
FIG. 1 is a diagram showing a construction of a liquid component sensor.

As shown in FIG. 1, a liquid component sensor 10 includes a light source 11, a detection cell 12, a spectrometer 13 and a light detector 14. A reference numeral 100 represents liquid. The detection cell has a specific structure. The structure other than the detection cell will be explained as follows.

The light source 11 outputs infrared light. The light source 11 corresponds to an infrared light source. Here, the light source for outputting infrared light may irradiate light including infrared light in certain wavelength zone. Thus, the light source may output only the infrared light. Alternatively, the light source may output both of the infrared light and visible light. In the present embodiment, the light source 11 is a thermal type optical source for outputting light including the mid-infrared light and visible light in a certain wavelength zone.

The spectrometer 13 disperses light, which passes through the detection cell 12. The spectrometer 13 may be a conventional spectroscopic element such as a diffraction grating, or a conventional interferometer such as a Fabry-Perot interferometer. In the present embodiment, the spectrometer 13 is the Fabry-Perot interferometer.

The light detector 14 detects light, which is dispersed by the spectrometer 13. The light detector 14 may be a conventional element such as thermocouple detector for detecting heat, which is generated by light radiation of the infrared light. In the present embodiment, the light detector 14 is the thermocouple detector.

Next, the detection cell 12 will be explained.

Figure 2:
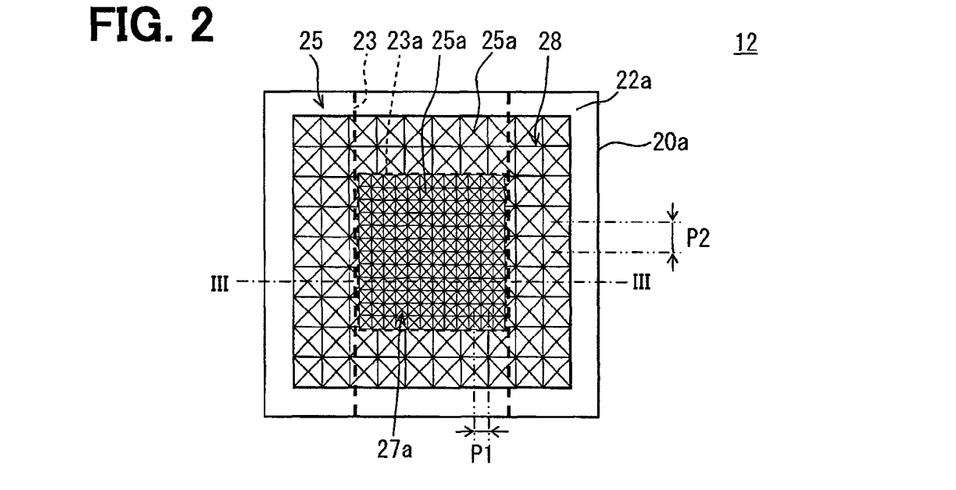
FIG. 2 is a diagram showing a plan view of a detection cell.
Figure 3:
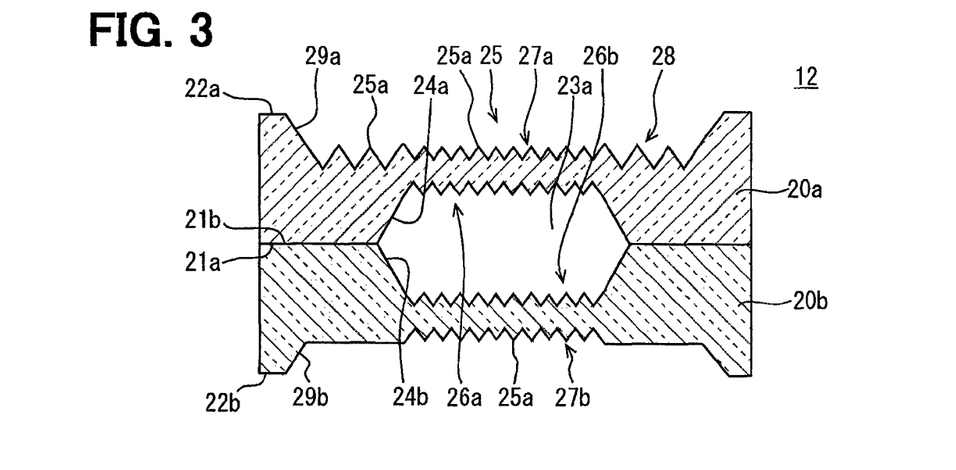
FIG. 3 is a diagram showing a cross sectional view of the detection cell taken along line in FIG. 2.

The detection cell 12 includes two substrates 20a, 20b, which are stacked. Each substrate 20a, 20b is made of material, which is an infrared light transmissive property. A stacking direction of the substrates 20a, 20b substantially coincides with an irradiation direction of light. The substrate 20a, 20b may be made of silicon substrate or a germanium substrate, which transmits the infrared light (specifically, mid-infrared light) therethrough.

In the present embodiment, each substrate 20a, 20b is made of silicon. Outer shapes and dimensions of the substrates 20a, 20b substantially coincide with each other. The first substrate 20a has two surfaces 21a, 22a, and the second substrate 20b has two surfaces 21b, 22b. The surface 21a of the first substrate 20a faces the surface 21b of the second substrate 20b so that the surfaces 21a, 21b provide facing surfaces. The surfaces 22a, 22b provide surfaces of the detection cell 12. Accordingly, the surfaces 21a, 21b are referred as facing surfaces 21a, 21b. Two substrates 20a, 20b are directly bonded to each other so that two substrates 20a, 20b provide an integrated substrate.

The detection cell 12 includes a passage 23 for flowing the liquid 100 therethrough. The passage 23 includes a wall, which is provided by the facing surface 21a of the first substrate 20a and the facing surface 21b of the second substrate 20b. Specifically, the passage 23 is formed between the facing surfaces 21a, 21b. At least a part of the passage 23 provides a detection portion 23a as a detecting region, at which the infrared light is irradiated toward the liquid 100.

In the present embodiment, a concavity 24a is formed at a part of the facing surface 21a of the first substrate 20a. Another concavity 24b is formed at a part of the facing surface 21b of the second substrate 20b. The concavity 24a corresponds to another concavity 24b. The passage 23 is formed by the wall of the concavity 24a on the facing surface 21a and the wall of the concavity 24b of the facing surface 21b. The passage 23 extends along one direction, which passes through a center of a plane perpendicular to the stacking direction, shown as a broken line in FIG. 2. The passage 23 has both ends, which open on two sides of the detection cell 12. The two sides of the detection cell 12 are opposite to each other. The detection cell 12 has an outer shape of a square in plan view. One end of the passage 23 is an introduction opening of the liquid 100 to the passage 23, and the other end of the passage 23 is a discharge opening of the liquid 100. The detection portion 23a is disposed at a center portion of the substrates 20a, 20b, which is surrounded with the broken line in FIG. 2.

The detection cell 12 includes a filter 25 for filtering the infrared light having a predetermined wavelength selectively on at least one of four surfaces 21a, 21b, 22a, 22b. The filter 25 is arranged on at least a part, which corresponds to the detection portion 23a.

In four filters 25 are arranged on four surfaces 21a, 21b, 22a, 22b, respectively. The filter 25 has a moth eye structure portion 26a, 26b, 27a, 27b, 28, which provides multiple protrusions 25a having a pyramid shape. Multiple protrusions 25a are arranged at predetermined pitches. The first moth eye structure portion 26a is formed on a part of the bottom of the concavity 24a corresponding to the detection portion 23a. The second moth eye structure portion 26b is formed on a part of the bottom of the concavity 24b corresponding to the detection portion 23a. The moth eye structure portion 27a is formed on a part of the surface 22a of the first substrate 20a corresponding to the detection portion 23a. Specifically, the concavity 29a is formed on the surface 22a, and the moth eye structure portion 27a is formed on a part of the bottom of the concavity 29a corresponding to the detection portion 23a. The moth eye structure portion 27b is formed on a part of the surface 22b of the second substrate 20b corresponding to the detection portion 23a. Specifically, the concavity 29b is formed on the surface 22b, and the moth eye structure portion 27b is formed on a part of the bottom of the concavity 29b corresponding to the detection portion 23a. Four moth eye structure portions 26a, 26b, 27a, 27b are referred as four inner potions, respectively. The moth eye structure portion 28 is formed on an outer periphery, which surrounds the detection portion 23a. Thus, the moth eye structure portion 28 is referred as an outer portion. In the present embodiment, the outer portion as the moth eye structure portion 28 is formed only on the surface 22a of the first substrate 20a. Specifically, the moth eye structure portion 28 is formed on the outer periphery of the bottom of the concavity 29a other than the detection portion 23a.

The protrusions 25a are arranged at every predetermined pitch P1 on the moth eye structure portions 26a, 26b, 27a, 27b as the inner portion. The predetermined pitch P1 is defined by micrometers. The protrusions 25a are arranged at every predetermined pitch P2, which is larger than the pitch P1, on the moth eye structure portion 28 as the outer portion. The predetermined pitch P2 is defined by micrometers. In the present embodiment, the pitch P1 is set to be equal to or larger than 3/N and smaller than 10/N (i.e., 3/N<=P1<10/N) when the substrates 20a, 20b has the refraction index defined as N. The pitch P2 is set to be equal to or larger than 10/N (i.e., P2>=10/N). Here, the refraction index of silicon is 3.43, and the refraction index of germanium is 4.0. As described above, each moth eye structure portion 26a, 26b, 27a, 27b, 28 is formed on the bottom of the concavity 24a, 24b, 29a, 29b. The protrusions 25a on each moth eye structure portion 26a, 26b, 27a, 27b, 28 have protrusion tops, each of which is lower than a periphery portion of the concavity 24a, 24b, 29a, 29b on the surface 21a, 21b, 22a, 22b of the substrate 20a, 20b.

Next, a manufacturing method of the detection cell 12 in the liquid component sensor 10 will be explained as follows.

Figure 4A:
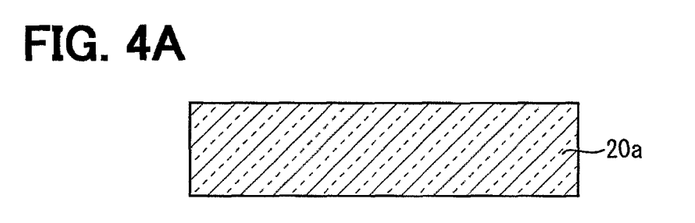
FIGS. 4A to 4D are diagrams showing a manufacturing method of the detection cell.
Figure 4B:
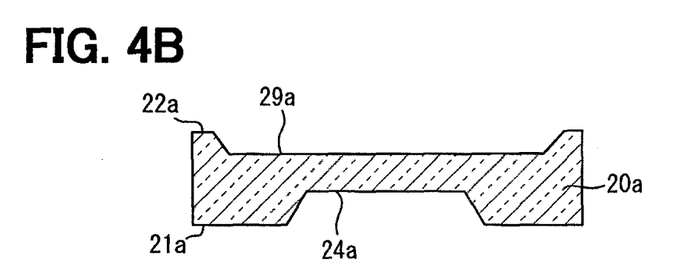
Figure 4C:
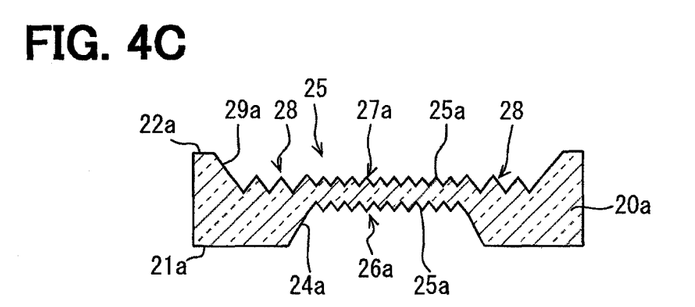

FIGS. 4A to 4C show a forming process of the first substrate 20a. First, as shown in FIG. 4A, the first substrate 20a having a plate shape is prepared. As shown in FIG. 4B, the concavities 24a, 29a are formed on both surfaces 21a, 21b of the first substrate 20a, respectively. In the present embodiment, the first substrate 20a is made of silicon. The concavities 24a, 29a are formed with utilizing a difference of etching speed depending on crystallographic plane.

Next, as shown in FIG. 4C, the moth eye structure portions 26a, 27a, 28 are formed on the bottom of the concavities 24a, 29a, respectively. The moth eye structure portions 26a, 27a, 28 provide the filter 25. The filter 25 is formed by a process shown in FIGS. 5A to 5D.

Figure 5A:
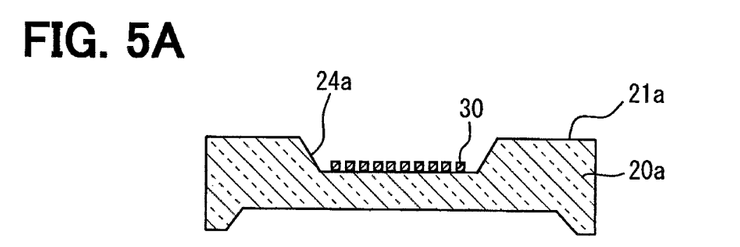
FIGS. 5A to 5D are diagrams showing a forming step of a moth eye structure portion.
Figure 5B:
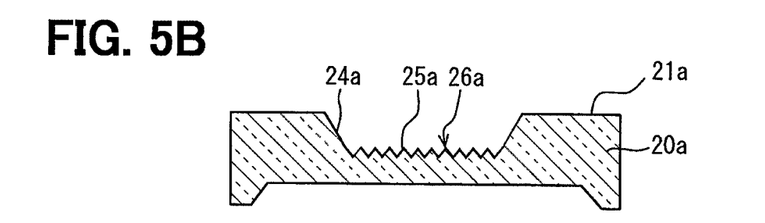

As shown in FIG. 5A, the mask 30 having a predetermine pattern is formed on the bottom of the concavity 24a. Then, as shown in FIG. 5B, with using the mask 30, the bottom is etched by a dry etching method such as a reactive ion etching method. Thus, the moth eye structure portion 26a having the protrusions 25a, which are arranged at every pitch P1, is formed.

Figure 5C:
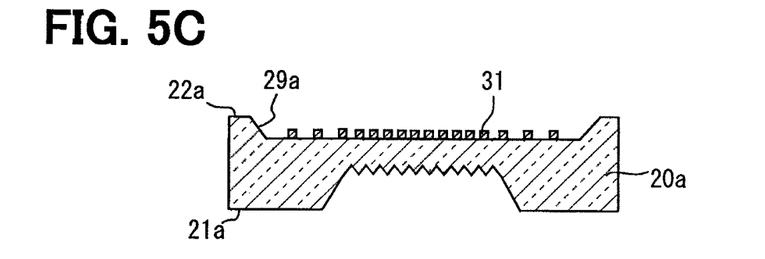
Figure 5D:
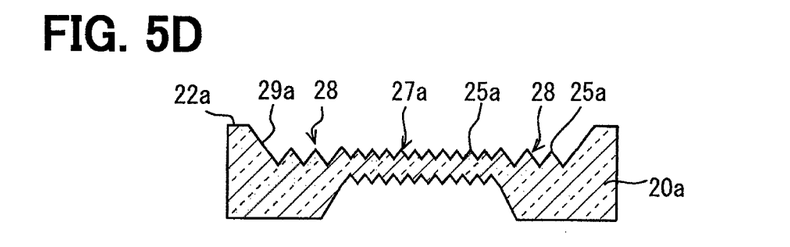

Next, as shown in FIG. 5C, a mask 31 having a predetermined pattern is formed on the bottom of the concavity 29a. In this case, a width of an opening corresponding to the outer portion as the moth eye structure portion 28 is set to be larger than that corresponding to the inner portion as the moth eye structure portion 27a. As shown in FIG. 5D, with using the mask 31, the bottom of the concavity 29a is etched by a dry etching method such as a reactive etching method (a RIE method). Thus, the moth eye structure portion 27a as the inner portion having the protrusions 25a, which are arranged at ever pitch P1, is formed. Further, the moth eye structure portion 258 as the outer portion having the protrusions 25a, which are arranged at every pitch P2, is formed. Here, because of the RIE lag, the outer portion corresponding to the larger width of the opening of the mask 31 is etched deeply so that the height of the protrusion 25a becomes large.

Here, the forming order of the moth eye structure portions 26a, 27a, 28 may be arbitrarily selected. Thus, the moth eye structure portion 26a may be formed on the surface 21a first, and the moth eye structure portions 27a, 28 may be formed on the surface 22a second. Alternatively, the moth eye structure portions 27a, 28 may be formed on the surface 22a first, and the moth eye structure portion 26a may be formed on the surface 21a second. The second substrate 20b is also processed according to a method similar to the above method. In this case, the moth eye structure portion is not formed on an outer periphery of the second substrate 20b.

Figure 4D:
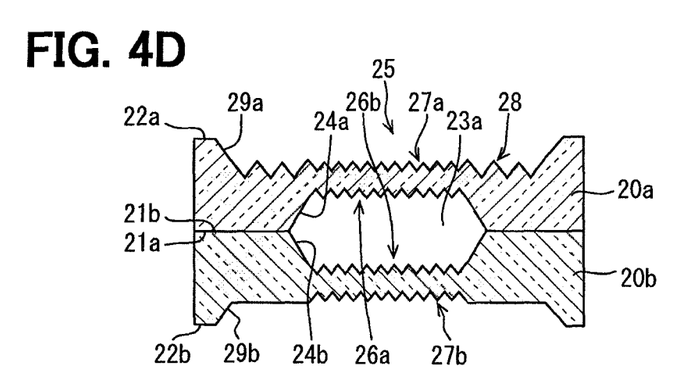

In FIG. 4D, the substrates 20a, 20b are bonded to each other. Specifically, the facing surfaces 21a, 21b face each other so as to adjust to each other, and then, the facing surfaces 21a, 21b are directly bonded to each other. Although the substrates 20a, 20b are bonded by a direct bonding method, alternatively, they may be bonded by an adhesive bonding method. Thus, the detection cell 12 is formed.

Next, the effects of the liquid component sensor 10 will be explained as follows.

In the present embodiment, the filter 25 is formed as a part of the detection cell 12. Accordingly, compared with a conventional detection cell, the number of elements in the liquid component sensor 10 is reduced. Further, since the filter 25 is formed as a part of the detection cell 12, compared with a case where the filter 25 is formed as an independent element from the detection cell 12, the position deviation of assembly is reduced. Further, the detection accuracy reduction caused by the position deviation is improved. Thus, the assembling process is easily simplified.

Figure 6:
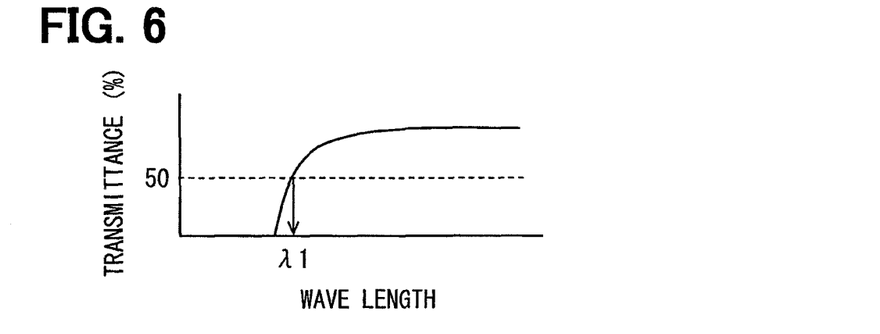
FIG. 6 is a graph showing an effect of the moth eye structure portion.

In the embodiment, the filter 25 has the moth eye structure portions 26a, 26b, 27a, 27b, 28, in which the protrusions 25a having the pyramid shape are arranged at every predetermined pitch. The moth eye structure portions 26a, 26b, 27a, 27b, 28 provide a high antireflection effect with respect to the light having a wavelength equal to or larger than a predetermined wavelength $\lambda 1$, as shown in FIG. 6. Accordingly, the transparent wavelength region is broadened, compared with a case where a anti reflection film for setting the optical length to be $\lambda \times \frac{1}{4}$ is formed on the surface of the substrates 20a, 20b. Further, the above anti reflection effect is obtained without depending on the material of the substrate 20a, 20b.

Figure 7:
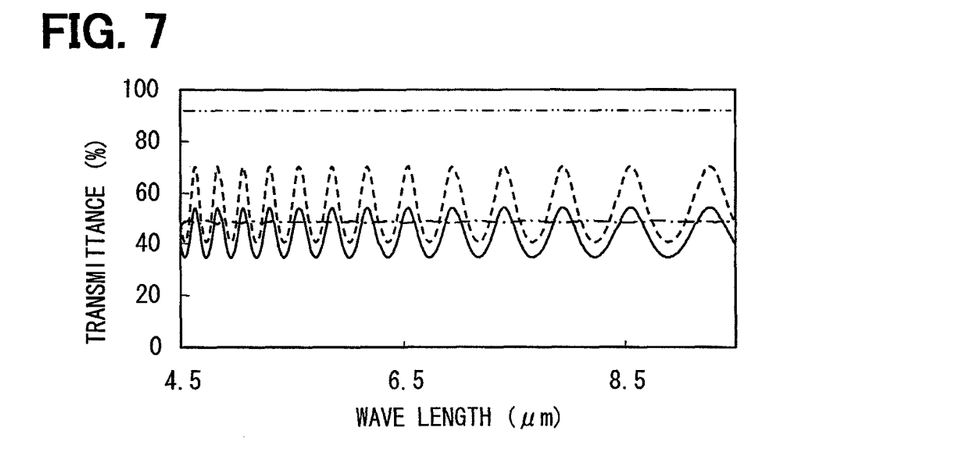
FIG. 7 is a graph showing an effect of an arrangement of the moth eye structure portion.

FIG. 7 shows a result of a simulation with respect to the effect of a forming place of the moth eye structure portion. In FIG. 7, the solid line represents a case where the sensor includes no moth eye structure portion. The broken line represents a case where the moth eye structure portion 27a, 27b is formed on only one of the surfaces 22a, 22a. The dashed dotted line represents a case where the moth eye structure portion 26a, 26b is formed on only one of the facing surfaces 21a, 21b. The dashed two dotted line represents a case where the moth eye structure portion 26a, 26b, 27a, 27b is formed on four surfaces 21a, 21b, 22a, 22b. In the simulation, the conditions other than the arrangement of the moth eye structure portions are the same. Here, the substrates 20a, 20b are made of silicon, and the liquid 100 includes mainly gasoline, which fills the passage 23 (i.e., the detection portion 23a).

As shown in the broken line in FIG. 7, when the moth eye structure portion 27a, 27b is formed on only one of the surfaces 22a, 22b, the transmittance increases by 15 percents, compared with a case where the sensor includes no moth eye structure portion. However, the amplitude of the interference wavelength (i.e., the strength change caused by the wavelength) is slightly increased, compared with a case where the sensor includes no moth eye structure portion. This is because the incident light amount to the detection portion 23a increases since the reflection loss is reduced on the surface 22a, 22b of the detection cell 12, so that the influence of the interference between the facing surfaces 21a, 21b is increased.

As shown in the dashed dotted line in FIG. 7, when the moth eye structure portion 26a, 26b is formed on only one of the facing surfaces 21a, 21b, the transmittance increases by 6 percents, compared with a case where the sensor includes no moth eye structure portion. The amplitude of the interference wavelength is much reduced. This is because the interference between the facing surfaces 21a, 21b, which face each other via a gap of the detection portion 23a, is restricted.

As shown in the dashed two dotted line in FIG. 7, when the moth eye structure portion 26a, 26b, 27a, 27b is formed on four surfaces 21a, 21b, 22a, 22b, the transmittance increases by 45 percents, compared with a case where the sensor includes no moth eye structure portion. Further, the amplitude of the waveform caused by the interference is substantially zero.

In view of the above simulation results, in the present embodiment, the moth eye structure portion 26a, 26b is formed on at least one of the facing surfaces 21a, 21b of the substrates 20a, 20b. Thus, when the moth eye structure portion 26a, 26b is formed on at least one of the wall for providing the detection portion 23a (i.e., the passage 23), the interference between the facing surfaces 21a, 21b is limited. Accordingly, the amplitude of the interference waveform of the light, which penetrates the detection cell 12 (i.e., the detection portion 23a), compared with a case where the moth eye structure portion 27a, 27b is formed on the surface 22a, 22b of the detection cell 12. Thus, the detection accuracy of the component and the concentration of the component in the liquid 100 is improved.

Further, the moth eye structure portion 27a, 27b is formed on at least one of the surfaces 22a, 22b of the detection cell 12. Here, the reflection loss at the boundary between the surface 22a, 22b of the detection cell 12 and the outside atmosphere such as air is larger than the boundary between the liquid 100 introduced into the passage 23 (i.e., the detection portion 23a) and the facing surface 21a, 21b. Thus, the reflection loss at the boundary between the detection cell 12 and the outside atmosphere is reduced. Thus, the light amount of the light to be entered into the detection portion 23a is increased, so that the sensitivity of the liquid component sensor 10 is improved.

Further, the moth eye structure portion 26a, 26b, 27a, 27b is formed on each of the surfaces 21a, 21b, 22a, 22b. Thus, the interference between the surfaces 21a, 21b, 22a, 22b is restricted, so that the amplitude of the interference waveform of the light penetrated the detection cell 12 is reduced. The reflection loss on the surface 21a, 21b, 22a, 22b is limited, so that the sensitivity of the liquid component sensor 10 is much improved.

In the present embodiment, the sensor includes the moth eye structure portions 26a, 26b, 27a, 27b as the inner portion corresponding to the detection portion 23a and the moth eye structure portion 28 as the outer portion corresponding to the outer periphery. The pitch P1 of the protrusions 25a on the moth eye structure portion 26a, 26b, 27a, 27b as the inner portion is smaller than the pitch P2 of the protrusions 25a of the moth eye structure portion 28 as the outer portion. When the pitch of the protrusions 25a becomes larger, the transparent wavelength region of the infrared light shifts to the long wavelength side. Accordingly, in the above construction, the predetermined wavelength λ1 at the moth eye structure portion 26a, 26b, 27a, 27b is shifted to the predetermined wavelength λ1 at the moth eye structure portion 28, so that only the infrared light irradiated on the detection portion 23a in a predetermined wavelength region penetrates. Therefore, the sensor having a simple structure provides the high detection accuracy.

In the present embodiment, the substrate 20a, 20b is made of silicon. When the substrate 20a, 20b is made of silicon, the corrosion resistance or the deliquescence resistance is improved, compared with a case where the substrate is made of a common fluorine compound, which transmits the infrared light therethrough. Further, since the cost of silicon is cheaper than a compound such as zinc sulfide (ZnS), the manufacturing cost of the sensor is reduced. Further, the filter 25 having the moth eye structure portion is formed by a conventional semiconductor process. Here, when the substrate 20a, 20b is made of germanium, similar effects are obtained. Further, since the absorption region of silicon is equal to or smaller than 1.1 micrometers, and another absorption region of silicon is equal to or larger than 10 micrometers. Thus, the light having a wavelength, which is not necessary or suitable for the analysis of the liquid 100, is eliminated by the detection cell 12, so that the detection accuracy is improved.

Figure 8:
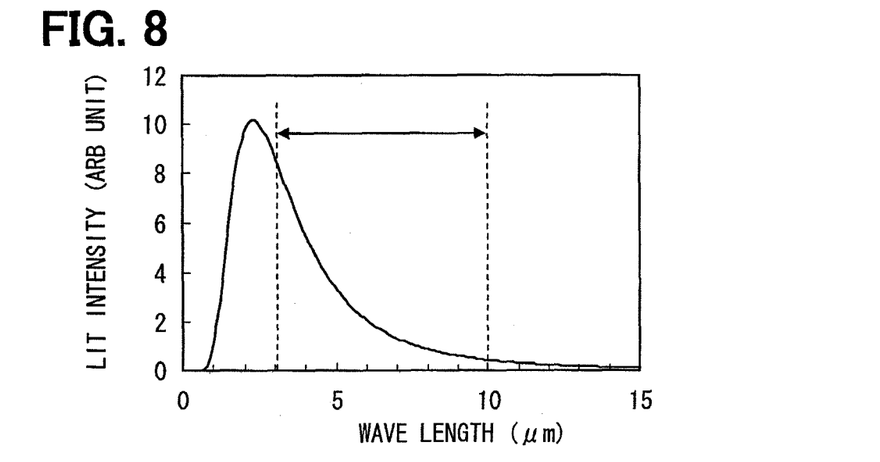
FIG. 8 is a graph showing a spectrum distribution of a thermal type light source.

Here, a peak of the absorption spectrum of the liquid 100 such as gasoline, alcohol such as ethanol, water and acetic acid is disposed in a region of the mid infrared light between 3 micrometers and 10 micrometers, which is shown as an arrow between broken lines in FIG. 8. Accordingly, the moth eye structure portions 26a, 26b, 27a, 27b are designed so as to set the wavelength λ1 corresponding to the high transmittance in a range between 3 micrometers and 10 micrometers.

Figure 9:
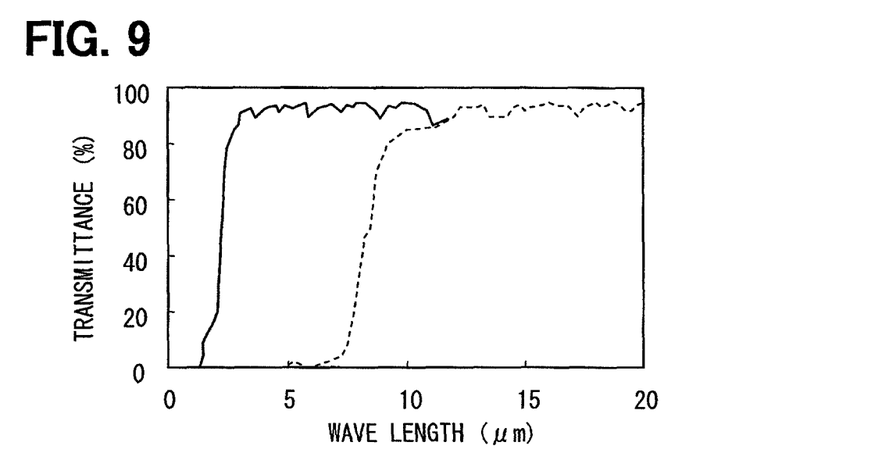
FIG. 9 is a graph sowing a relationship between wavelength corresponding to a high transmittance and a pitch.

In the present embodiment, the pitch P1 of the moth eye structure portions 26a, 26b, 27a, 27b is in a range between 3/N and 10/N (3/N<=P1<10/N). As described above, the refraction index of silicon as material of the substrates 20a, 20b is around 3.43, and the refraction index of germanium is around 4.0. Accordingly, when the pitch P1 is set in the above range, and the substrates 20a, 20b are made of silicon, the pitch P1 is in a range between 0.87 and 2.92. When the substrates 20a, 20b are made of germanium, the pitch P1 is in a range between 0.75 and 2.5. The relationship between the wavelength and the pitch is shown in FIG. 9. The solid line in FIG. 9 shows a case where the pitch is 0.9 micrometers, and the broken line shows a case where the pitch is 3 micrometers. As shown in FIG. 9, when the pitch P1 is set in the above range, the wavelength λ1 corresponding to the high transmittance of the moth eye structure portions 26a, 26b, 27a, 27b is in a range between 3 micrometers and 10 micrometers. Thus, the infrared light in a certain wavelength region corresponding to the peak of the absorption spectrum of the liquid 100 can penetrate the detection portion 23a. Accordingly, the component and the concentration of the component in the liquid 100 is detected easily.

In the present embodiment, the sensor 10 includes the thermal type light source 11. FIG. 8 shows a calculation result of the spectrum distribution when the temperature of the source 11 is 1000° C. As shown in FIG. 8, when the wavelength is 10 micrometers, the light intensity of light emitted from the light source 11 is smaller than that of light having the wavelength shorter than 10 micrometers. Accordingly, even if the light penetrates the detection portion, the detection accuracy is not substantially affected by the light having the wavelength equal to or longer than 10 micrometers. On the other hand, the pitch P2 of the moth eye structure portion 28 is equal to or larger than 10/N (i.e., P2>=10/N). When the pitch P2 is 3 micrometers, as shown in the broken line in FIG. 9, the wavelength λ1 corresponding to the high transmittance at the moth eye structure portion 28 is about 10 micrometers. Accordingly, when the pitch P2 is set in the above range, the detection accuracy is improved.

Figure 10:
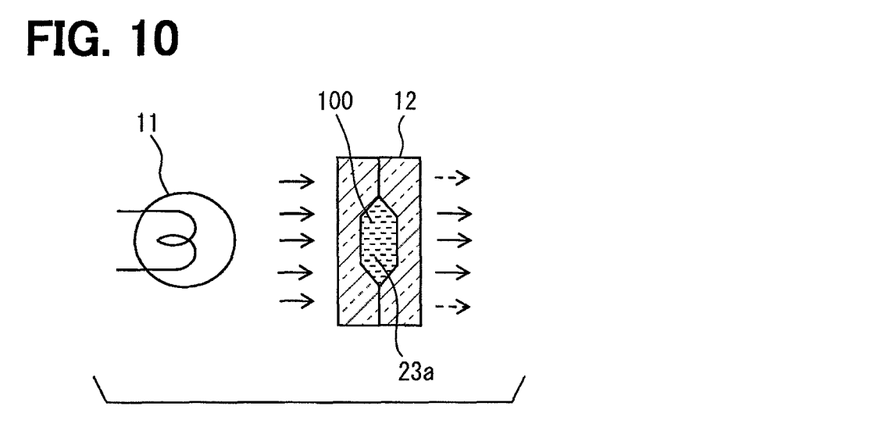
FIG. 10 is a diagram showing a change in light property after and before the detection cell.
Figure 11:
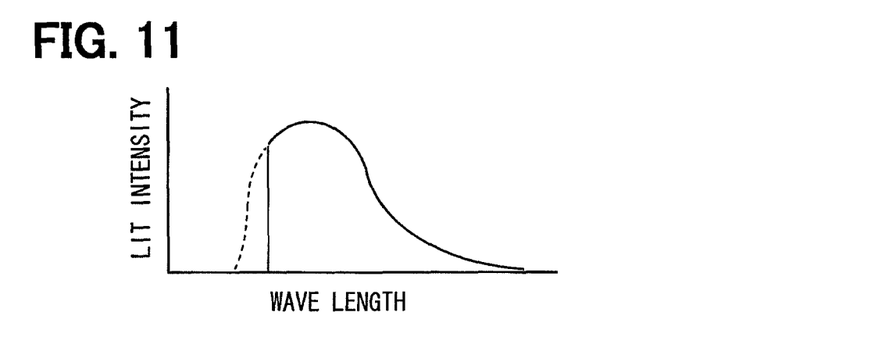
FIG. 11 is a graph showing a spectrum distribution of light passing through the detection cell.

When the pitches P1, P2 are set, as shown in FIG. 10, the light penetrating the detection cell 12 at the outer periphery has the wavelength equal to or larger than 10 micrometers. The light at a portion corresponding to the detection portion 23a has the wavelength shorter than the light penetrating the outer periphery. The spectrum distribution of light penetrating the detection cell 12 is shown in FIG. 11. Compared with FIG. 8, in FIG. 11, the light having the wavelength, which is not necessary for the analysis of the liquid 100, is cut by the filtering effect of the moth eye structure portions 26a, 26b, 27a, 27b. In FIG. 11, the broken line indicates the cut part of the light.

In the present embodiment, the moth eye structure portion 26a, 26b, 27a, 27b, 28 is formed on the bottom of the concavity 24a, 24b, 29a, 29b. The top end of the protrusion 25a on the moth eye structure portion 26a, 26b, 27a, 27b, 28 has a height lower than the periphery of the surface 21a, 21b, 22a, 22b of the substrate 20a, 20b around the concavity 24a, 24b, 29a, 29b. Accordingly, the protrusion of the moth eye structure portion 26a, 26b, 27a, 27b, 28 is protected from damage. Thus, the detection accuracy and the sensitivity are improved. Further, the handling of the sensor is improved.

In the above embodiment, the filter 25 is formed on each surface 21a, 21b, 22a, 22b of the substrates 20a, 20b. Alternatively, the filter 25 may be formed on only one surface 21a, 21b, 22a, 22b.

Figure 12:
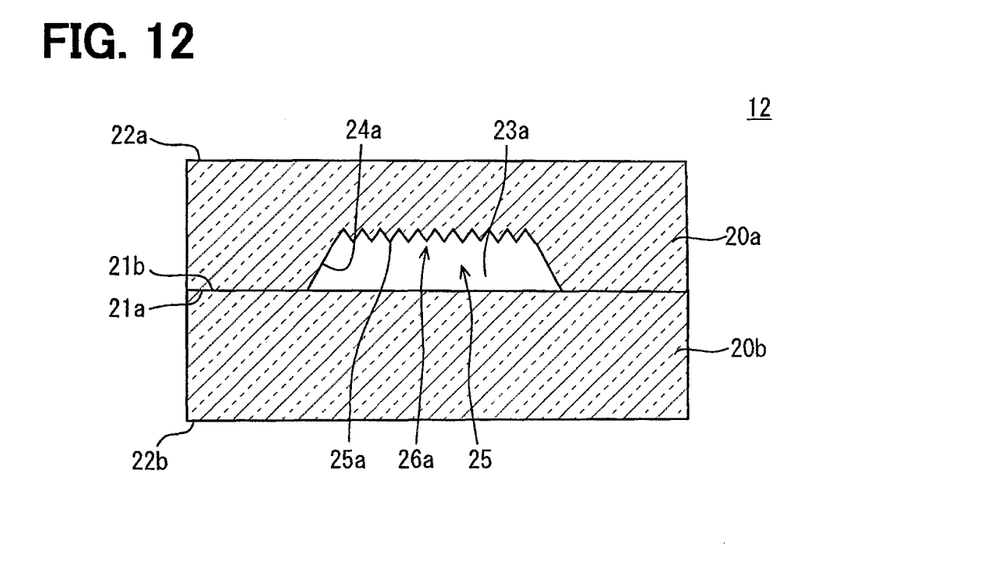
FIG. 12 is a diagram showing a cross sectional view of a detection cell according to a first modification.

FIG. 12 shows a first modification of the embodiment. In FIG. 12, the moth eye structure portion 26a as the filter 25 is formed on only the bottom of the concavity 24a, which is formed on the facing surface 21a of the substrate 20a. When the moth eye structure portion 26a, 26b is formed on at least one of the facing surfaces 21a, 21b, the amplitude of the interference waveform of the light penetrating the detection cell 12 is reduced.

Figure 13:
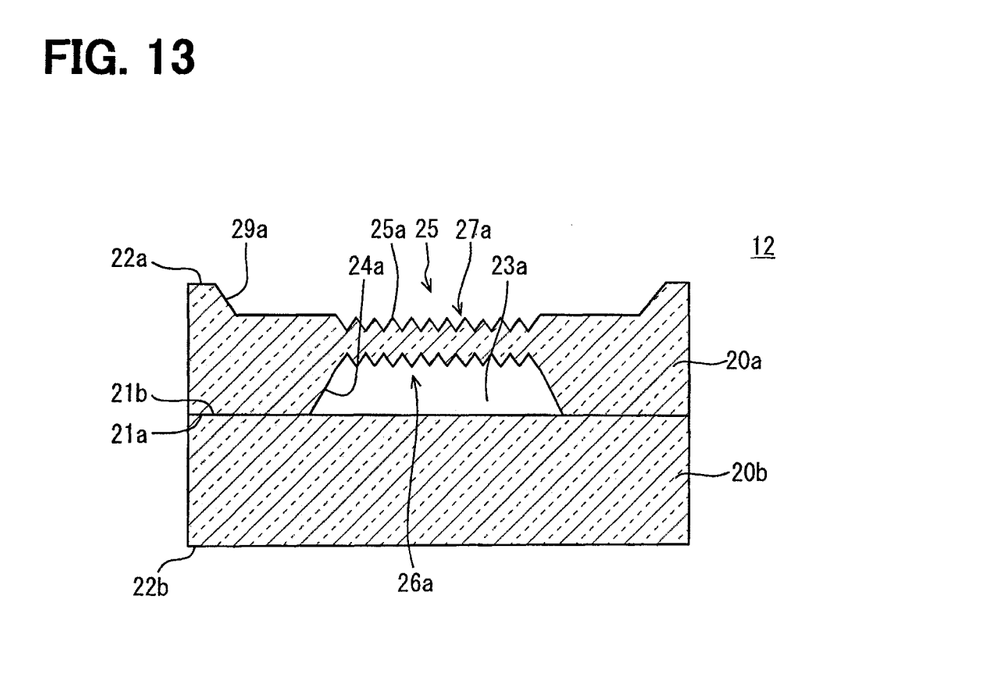
FIG. 13 is a diagram showing a cross sectional view of a detection cell according to a second modification.

FIG. 13 shows a second modification of the embodiment. In FIG. 13, the moth eye structure portion 26a is formed on the bottom of the concavity 24a. Further, the moth eye structure portion 27a is formed on the surface 22a of the first substrate 20a. When the moth eye structure portion 27a, 27b is formed on at least one of the surfaces 22a, 22b of the substrates 20a, 20b, the strength of light penetrating the detection portion 23a is increased. Specifically, when the detection portion 23a has the structure in FIG. 13, the amplitude of the interference waveform of the light penetrating the detection cell 12 is reduced, and further, the intensity of light is increased. Alternatively, the moth eye structure portion 27a, 27b may be formed on only one surface 22a, 22b of the substrate 20a, 20b without forming the moth eye structure portion 26a on the bottom of the concavity 24a.

Figure 14:
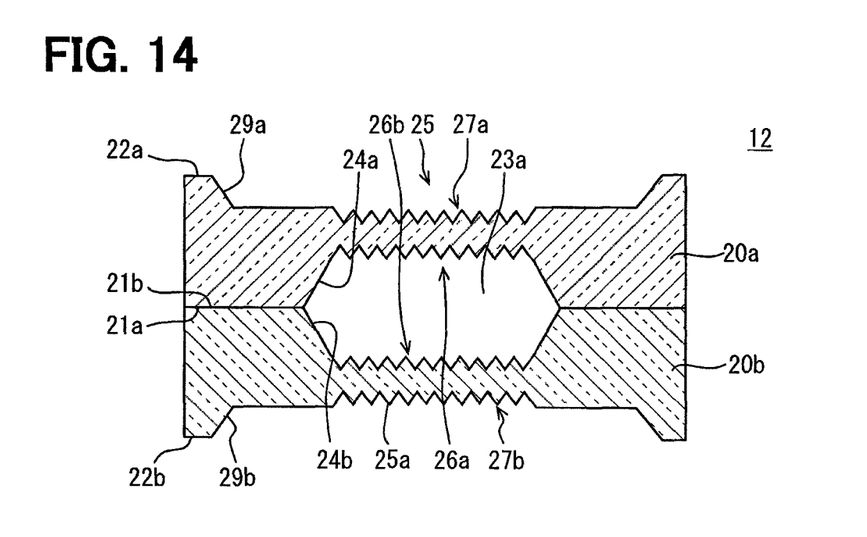
FIG. 14 is a diagram showing a cross sectional view of a detection cell according to a third modification.

FIG. 14 shows a third modification of the embodiment. In FIG. 14, the sensor does not have the outer periphery portion. Thus, the filter 25 is formed on each of the surfaces 21a, 21b, 22a, 22b, and the filter 25 is not formed on the outer periphery. Further, in the above embodiment, the moth eye structure portion 28 is formed on only the surface 22a of the first substrate 20a. Alternatively, the moth eye structure portion may be formed on the surface 22b of the second substrate 20b.

Figure 15:
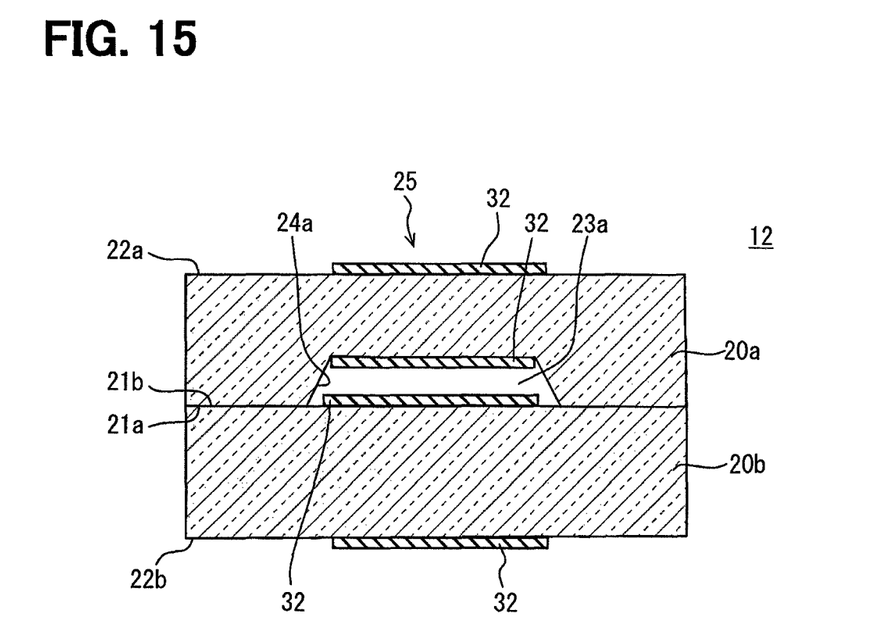
FIG. 15 is a diagram showing a cross sectional view of a detection cell according to a fourth modification.

FIG. 15 shows a fourth modification of the embodiment. An anti reflection film 32 is formed as the filter 25. The anti reflection film 32 is formed on both surfaces 21a, 22a, 21b, 22b of at least one substrate 20a, 20b. The anti reflection film 32 includes a low refraction index film and a high refraction index film, which are stacked. The film thickness of each of the low refraction index film and the high refraction index film is about the optical length of $\lambda \times \frac{1}{4}$ when the light has the wavelength of $\lambda$. Thus, the anti reflection film 32 is a multi-layered filter. When the substrates 20a, 20b are made of silicon, the filter may include a silicon dioxide film and a silicon film, which are stacked. Here, the silicon dioxide film contacts the substrate 20a, 20b. Alternatively, the anti reflection film 32 may be a single layer film having a thickness of the optical length of $\lambda \times \frac{1}{4}$ when the light has the wavelength of $\lambda$. When the substrates 20a, 20b are made of silicon, the anti reflection film 32 may be a silicon dioxide film. In FIG. 15, the filter 25 is formed on the first substrate 20a and the second substrate 20b.

In the above embodiment, the opening is formed on the side of the detection cell 12 so that both ends of the passage 23 are opened. Alternatively, the sensor may include only the detection portion 23a for providing the passage 23. A through hole for introducing the liquid and connecting to the detection portion 23a and a through hole for discharging the liquid may be formed on at least one of the substrates 20a, 20b.

In the above embodiment, the concavities 24a, 24b formed on the substrates 20a, 20b provide the passage 23. Alternatively, as shown in FIGS. 12, 13 and 15, the wall of the concavity 24a formed on one substrate 20a and the flat facing surface 21b of the other substrate 20b may provide the passage 23.

In the above embodiment, the concavity 29a, 29b is disposed on the surface 22a, 22b of the detection cell 12. The moth eye structure portion 27a, 27b, 28 is formed on the bottom of the concavity 29a, 29b. Alternatively, the sensor may not include the concavity 29a, 29b, and the moth eye structure portion 27a, 27b, 28 may be formed on the flat surface 22a, 22b. Alternatively, the moth eye structure portion 26b may be formed on the flat facing surface 21b, which provides the passage 23.

The above disclosure has the following aspects.

According to an example aspect of the present disclosure, a liquid component sensor includes: an infrared light source; a detection cell, which includes: a pair of substrates made of material for penetrating an infrared light therethrough and stacked each other; a passage for flowing liquid arranged between facing surfaces of the substrates; and a detection portion for detecting the liquid provided by at least a part of the passage; a spectrometer for dispersing light penetrating the detection cell; and a light detector for detecting dispersed light. Each substrate includes an outside surface and the facing surface, which faces another substrate, and the outside surface is opposite to the facing surface, so that the pair of substrates provide four surfaces totally. The detection cell further includes a filter for passing the infrared light having a predetermined wavelength selectively. The filter is disposed on at least one of four surfaces at a predetermined position, which corresponds to at least the detection portion.

In the above sensor, the filter is a part of the detection cell. Thus, the number of elements in the sensor is minimized, compared with a conventional detection cell. Further, a position deviation of the filter when the sensor is assembled is restricted, compared with a case where the filter is assembled on the detection cell as a separate element. Thus, the detection accuracy reduction caused by the position deviation is limited. Therefore, the assembling of the sensor is simplified.

Alternatively, the filter may include a moth eye structure portion, which has a plurality of protrusions arranged at predetermined pitches. In this case, the moth eye structure portion provides high anti reflection effect with respect to light having a wavelength equal to or longer than a predetermined wavelength, compared with a case where the filter is provided by an anti reflection film. Thus, the transparent wavelength region is expanded, compared with an anti reflection film structure. Here, this effect does not depend on the material of the substrate substantially.

Alternatively, the moth eye structure portion may be disposed on at least one of the facing surfaces of the substrates. In this case, the interference between the facing surfaces is restricted. Accordingly, the amplitude of an interference waveform of light, which penetrates the detection cell, is reduced, so that an intensity change over wavelength is reduced. Thus, the detection accuracy of the component and the concentration of the component is improved.

Alternatively, the moth eye structure portion may be disposed on at least one of the outside surfaces of the substrates. The reflection loss at the boundary between the outside surface of the detection cell and the outside atmosphere is larger than the boundary between the liquid introduced into the passage and the facing surface. Thus, the reflection loss at the boundary between the outside surface of the detection cell and the outside atmosphere is reduced, so that the sensitivity is improved.

Alternatively, the moth eye structure portion may be disposed on each of the facing surfaces and the outside surfaces of the substrates. In this case, the interference among four surfaces is limited, so that the amplitude of an interference waveform of light, which penetrates the detection cell, is much reduced. Further, the reflection loss at each surface is limited, so that the detection sensitivity is improved.

Alternatively, the moth eye structure portion may include an inner portion and an outer portion. The inner portion is disposed at the predetermined position, which corresponds to the detection portion. The outer portion surrounds the inner portion. The inner portion has a plurality of protrusions arranged at predetermined first pitches; and the outer portion has a plurality of protrusions arranged at predetermined second pitches, each of which is larger than the first pitch. When the pitch of the protrusions becomes larger, the transparent wavelength region of the infrared light shifts to the longer wavelength side. Accordingly, only the infrared light in a certain wavelength range, which is irradiated on the detection portion, passes through the detection portion. Thus, it is not necessary to focus the light on the detection portion. The sensor having the high detection accuracy is easily manufactured.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

What is claimed is:

1. A liquid component sensor comprising:
an infrared light source;
a detection cell, which includes: a pair of substrates made of material for penetrating an infrared light therethrough and stacked each other; a passage for flowing liquid arranged between facing surfaces of the substrates; and a detection portion for detecting the liquid provided by at least a part of the passage;
a spectrometer for dispersing light penetrating the detection cell; and
a light detector for detecting dispersed light, wherein:
each substrate includes an outside surface and the facing surface, which faces another substrate, and the outside surface is opposite to the facing surface, so that the pair of substrates provide four surfaces totally;
the detection cell further includes a filter for passing the infrared light having a predetermined wavelength selectively;
the filter is disposed on at least one of four surfaces at a predetermined position, which corresponds to at least the detection portion;
the filter includes a moth eye structure portion, which has a plurality of protrusions arranged at predetermined pitches;
the moth eye structure portion includes an inner portion and an outer portion;
the inner portion is disposed at the predetermined position, which corresponds to the detection portion;
the outer portion surrounds the inner portion;
the inner portion has a plurality of protrusions arranged at predetermined first pitches; and
the outer portion has a plurality of protrusions arranged at predetermined second pitches, each of which is larger than the first pitch.

2. The liquid component sensor according to claim 1, wherein:
the moth eye structure portion is disposed on at least one of the facing surfaces of the substrates.

3. The liquid component sensor according to claim 1, wherein:
the moth eye structure portion is disposed on at least one of the outside surfaces of the substrates.

4. The liquid component sensor according to claim 1, wherein:
the moth eye structure portion is disposed on each of the facing surfaces and the outside surfaces of the substrates.

5. The liquid component sensor according to claim 1, wherein:
the substrate, on which the inner portion is disposed, has a refraction index referred as N;
the first pitch is equal to or larger than $3/N$;
the first pitch is smaller than $10/N$; and
the first pitch is defined by micrometer.

6. The liquid component sensor according to claim 5, wherein:
the infrared light source is a thermal type light source;
the second pitch is equal to or larger than $10/N$; and
the second pitch is defined by micrometer.

7. The liquid component sensor according to claim 1, wherein:
the moth eye structure portion is arranged on a bottom of a concavity, which is disposed on the at least one of four surfaces of the substrates.

8. The liquid component sensor according to claim 1, wherein:
each substrate is made of silicon.

9. The liquid component sensor according to claim 1, wherein:
each substrate is made of germanium.

* * * * *